(12) United States Patent
Coates et al.

(10) Patent No.: US 6,175,014 B1
(45) Date of Patent: Jan. 16, 2001

(54) PROCESS FOR THE PREPARATION OF LACTAM DERIVATIVES

(75) Inventors: Ian Harold Coates, Hertford; Alexander William Oxford; Peter Charles North, both of Royston; Thomas Miller, Herefield; Anthony David Baxter, Iver Heath; Kevin Ian Hammond, Ulverston, all of (GB)

(73) Assignee: Glaxo Group Limited, Greenford (GB)

( * ) Notice: Under 35 U.S.C. 154(b), the term of this patent shall be extended for 0 days.

(21) Appl. No.: 08/137,228

(22) Filed: Oct. 18, 1993

Related U.S. Application Data

(63) Continuation of application No. 08/033,469, filed on Mar. 18, 1993, now abandoned, which is a continuation of application No. 07/785,258, filed on Nov. 4, 1991, now abandoned, which is a continuation of application No. 07/485,534, filed on Feb. 27, 1990, now abandoned.

(30) Foreign Application Priority Data

Feb. 28, 1989 (GB) .................................. 8904552

(51) Int. Cl.[7] ...................... C07D 233/61; C07D 471/04
(52) U.S. Cl. ................................ 546/84; 546/85; 546/86; 546/87; 548/335.5; 548/429
(58) Field of Search ............................... 546/84; 540/524

(56) References Cited

U.S. PATENT DOCUMENTS 4,859,662 * 8/1989 Coates et al. ..................... 548/336

FOREIGN PATENT DOCUMENTS

| 3 740 352 | 9/1988 | (DE) . |
|---|---|---|
| 0306323 | 8/1989 | (EP) . |
| 0353983 | 7/1990 | (EP) . |
| 2209335 * | 5/1989 | (GB) . |

OTHER PUBLICATIONS

Challis et al. Comprehensive Org. Chem., Pergamon Press 1979, vol. 2, Chapter 9, p. 1015.*
Challis et al. The Chemistry of Amides, Interscience Publishers 1970, Chapter 13, p. 753–754.*
Prelog et al. Helv. Chim. Acta, 1959, 42, 1301–1309.*
Theilacker et al. Annalen der Chemie, 1953, 584, 87–95.*

* cited by examiner

Primary Examiner—Joseph K. McKane
Assistant Examiner—Jane C. Oswecki
(74) Attorney, Agent, or Firm—Bacon & Thomas

(57) ABSTRACT

The invention provides a process for the preparation of a compound of general formula (I):

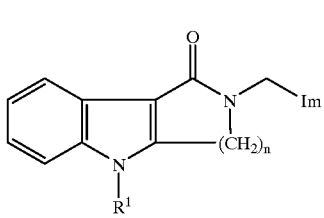

(I)

wherein Im represents an imidazolyl group of the formula:

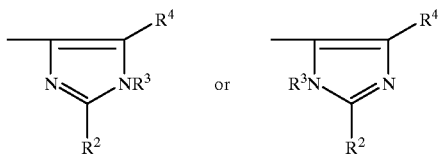

and $R^1$ represents a hydrogen atom or a group as herein defined including —$CO_2R^5$, —$COR^5$, —$CONR^5R^6$ or —$SO_2R^5$ wherein $R^5$ and $R^6$, which may be the same or different, are as herein defined with the proviso that $R^5$ does not represent a hydrogen atom when $R^1$ represents a group —$CO_2R^5$ or —$SO_2R^5$; one of the groups represented by $R^2$, $R^3$ and $R^4$ is a hydrogen atom or a $C_{1-6}$alkyl, $C_{3-7}$cycloalkyl, $C_{3-6}$alkenyl, phenyl or phenyl $C_{1-3}$alkyl group, and each of the other two groups, which may be the same or different, represents a hydrogen atom or a $C_{1-6}$alkyl group; and n represents 2 or 3; which comprises reacting a compound of formula (II)

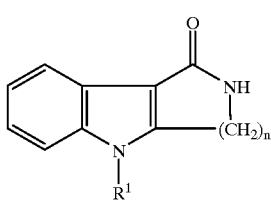

(II)

or a protected derivative thereof, with a compound of formula (III):

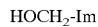

(III)

or a salt thereof in the presence of an acid at an elevated temperature, followed where necessary by removal of any protecting groups.

8 Claims, No Drawings

PROCESS FOR THE PREPARATION OF LACTAM DERIVATIVES

This application is a CONTINUATION of application Ser. No. 08/033,469, filed Mar. 18, 1993, now abandoned, which is a CONTINUATION of application Ser. No. 07/785,258, filed Nov. 4, 1991, now abandoned, which is a CONTINUATION of application Ser. No. 07/485,534, filed Feb. 27, 1990, now abandoned.

This invention relates to a process for the preparation of heterocyclic compounds.

In British patent application no. 2209335A, which was unpublished at the priority date of the present application, a group of lactam derivatives are described which may be represented by the general formula (I):

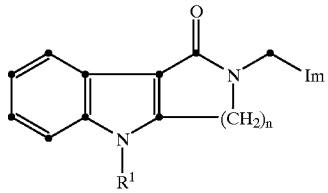

wherein Im represents an imidazolyl group of the formula:

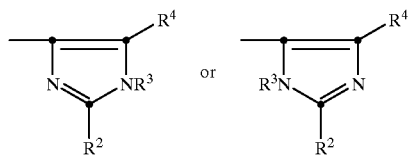

and $R^1$ represents a hydrogen atom or a group selected from $C_{1-6}$alkyl, $C_{3-6}$alkenyl, $C_{3-10}$alkynyl, $C_{3-7}$cycloalkyl, $C_{3-7}$cycloalkyl $C_{1-4}$alkyl, phenyl, phenyl $C_{1-3}$alkyl, phenylmethoxymethyl, phenoxyethyl, phenoxymethyl, —$CO_2R^5$, —$COR^5$, —$CONR^5R^6$ or —$SO_2R^5$ (wherein $R^5$ and $R^6$, which may be the same or different, each represents a hydrogen atom, a $C_{1-6}$ alkyl or $C_{3-7}$cycloalkyl group, or a phenyl or phenyl $C_{1-4}$alkyl group, in which the phenyl group is optionally substituted by one or more $C_{1-4}$alkyl, $C_{1-4}$alkoxy or hydroxy groups or halogen atoms, with the proviso that $R^5$ does not represent a hydrogen atom when $R^1$ represents a group —$CO_2R^5$ or —$SO_2R^5$);

one of the groups represented by $R^2$, $R^3$ and $R^4$ is a hydrogen atom or a $C_{1-6}$alkyl, $C_{3-7}$cycloalkyl, $C_{3-6}$alkenyl, phenyl or phenyl $C_{1-3}$alkyl group, and each of the other two groups, which may be the same or different, represents a hydrogen atom or a $C_{1-6}$alkyl group;

n represents 2 or 3;

and physiologically acceptable salts and solvates thereof.

Several processes for the preparation of these compounds are described in the abovementioned British patent application.

As described in British patent application no. 2209335A, the compounds of formula (I) are potent and selective antagonists of 5-hydroxytryptamine (5-HT) at 5-HT$_3$ receptors. They are useful in the treatment of conditions such as psychotic disorders (e.g. schizophrenia and mania); anxiety; and nausea and vomiting, particularly that associated with cancer chemotherapy and radiotherapy.

The present invention provides a process for the preparation of a compound of general formula (I) which comprises reacting a compound of formula (II):

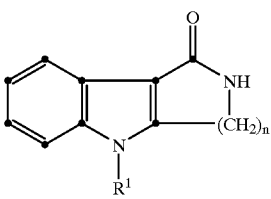

or a protected derivative thereof, with a compound of formula (III):

HOCH$_2$-Im    (III)

or a salt thereof, in the presence of an acid at an elevated temperature, followed where necessary by removal of any protecting groups.

The acid may be, for example, a strong mineral acid (e.g. hydrochloric acid), a hydrocarbylsulphonic acid (e.g. p-toluenesulphonic or methanesulphonic acid), or a carboxylic acid (e.g. maleic or acetic acid).

The reaction may conveniently be effected in a high boiling polar solvent such as N-methylpyrrolidinone or dimethylacetamide, at an elevated temperature, for example in the range 100 to 200° C. Alternatively the reaction may be conveniently effected in water, an alcohol (e.g. isopropanol or n-butanol), xylene or acetic acid at the reflux temperature of the solvent.

According to one aspect of the invention, the acid may be, for example, a strong mineral acid (e.g. hydrochloric acid) or a hydrocarbylsulphonic acid (e.g. p-toluenesulphonic acid). According to another aspect of the invention, the reaction may be effected in water or an alcohol (e.g. isopropanol) at the reflux temperature of the solvent.

Most preferably, the reaction is effected in the presence of a hydrocarbylsulphonic acid (e.g. p-toluenesulphonic or methanesulphonic acid) or hydrochloric acid, in N-methylpyrrolidinone or dimethylacetamide at a temperature in the range 100 to 200° C., more preferably 100 to 150° C. The use of a hydrocarbylsulphonic acid (e.g. p-toluenesulophonic acid) is particularly preferred.

The compound of formula (III) is preferably used in the form of a salt, more particularly the hydrochloride salt. When the reaction is effected with the hydrochloride salt of a compound of formula (III), the addition of an acid is optional, since the hydrogen chloride associated with the compound of formula (III) provides sufficiently acidic conditions.

Compounds of formula (II) may be prepared, for example, by the method described in British patent application no. 2209335A. Compounds of formula (II) may be obtained by a Beckmann rearrangement of an oxime of formula (IV):

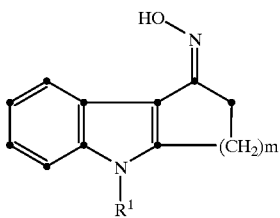

(IV)

wherein m represents 1 or 2, or a protected derivative thereof. The Beckmann rearrangement may be effected using conventional methods, for example by using an acid (e.g. polyphosphoric or sulphuric acid, or a mixture of hydrochloric acid, acetic anhydride and acetic acid) in an inert solvent such as an ether (e.g. dioxan), an amide (e.g. dimethylformamide) or a hydrocarbon (e.g. toluene or cyclohexane), at an elevated temperature of, for example, 50 to 120° C. Alternatively, the hydroxy group of the oxime of formula (IV), may be converted into a leaving group such as a chloride (using, for example, phosphorus pentachloride) or a hydrocarbylsulphonate (e.g. a mesylate or a tosylate) or a trifluoroacetate group (using conventional acylation methods). Subsequent heating at a temperature of, for example, 20 to 150° C., in an inert solvent as described above, gives a compound of formula (II).

Compounds of formula (III) are either known, or may be prepared from known compounds by conventional procedures.

Where a protected derivative of a compound of formula (II) is used in the above process, it may be a derivative in which the indole nitrogen atom is protected. The N-protecting group may be, for example, an arylmethoxymethyl (e.g. phenylmethoxymethyl) group. This group may be cleaved from a protected derivative of a compound of formula (I) by hydrogenolysis in the presence of a catalyst (e.g. palladium on charcoal).

Where it is desired to isolate a compound of formula (I) as a salt, for example a physiologically acceptable salt, e.g. a hydrochloride, this may be achieved by reacting the compound of formula (I) in the form of the free base with an appropriate acid, preferably with an equivalent amount, in a suitable solvent such as an alcohol (e.g. ethanol or methanol), an aqueous alcohol (e.g. aqueous ethanol), a halogenated hydrocarbon (e.g. dichloromethane), an ester (e.g. ethyl acetate), an ether (e.g. tetrahydrofuran) or a ketone (e.g. acetone). Alternatively, salt formation may take place in situ and the compound of formula (I) may be isolated directly from the reaction mixture in the form of a salt.

Physiologically acceptable salts may also be prepared from other salts, including other physiologically acceptable salts, of the compound of formula (I) using conventional methods.

Individual enantiomers of the compounds of the invention may be obtained by resolution of a mixture of enantiomers (e.g a racemic mixture) using conventional means, such as an optically active resolving acid; see for example 'Stereochemistry of Carbon Compounds' by E. L. Eliel (McGraw Hill, 1962) and 'Tables of Resolving Agents' by S. H. Wilen.

According to a preferred embodiment, the process of the invention may be used for the preparation of compounds of formula (I) in which $R^1$ represents a hydrogen atom or a $C_{1-3}$alkyl (e.g. methyl, ethyl, n-propyl or isopropyl) group, $R^2$ and $R^3$ represent hydrogen atoms, $R^4$ represents a methyl group and n represents 2.

More particularly the process of the present invention may be used to prepare 2,3,4,5-tetrahydro-5-methyl-2-[(5-methyl-1H-imidazol-4-yl)methyl]-1H-pyrido[4,3-b]indol-1-one and its physiologically acceptable salts (e.g. hydrochloride) and solvates.

The invention is illustrated by the following Examples which all describe the preparation of 2,3,4,5-tetrahydro-5-methyl-2-[(5-methyl-H-imidazol-4-yl)methyl]-1H-pyrido[4,3-b]indol-1-one (Compound X). All temperatures are in 0° C. Thin layer chromatography (t.l.c.) was carried out on silica. Solvent System A as used for t.l.c. denotes dichloromethane: ethanol: 0.88 ammonia solution.

$^1$H-N.m.r. spectra were obtained at 250 MHz for dilute solutions in $d_6$-dimethyl sulphoxide. Intermediate 1 denotes 2,3,4,5-tetrahydro-5-methyl-1H-pyrido[4,3-b]indol-1-one and Intermediate 2 denotes 4-hydroxymethyl-5-methylimidazole hydrochloride.

EXAMPLE 1

A mixture of Intermediate 1 (49.97 g), p-toluenesulphonic acid monohydrate (9.50 g) and Intermediate 2 (20.25 g) in N-methylpyrrolidinone (250 ml) was stirred and heated to 125° (over 1 h) The reaction was then heated at 125–130° for 4.5 h, during which time two further portions of Intermediate 2 (17.51 g and 6.88 g) were added. The reaction mixture was cooled, diluted with water (100 ml), and the stirred mixture was treated slowly with 8% aqueous sodium bicarbonate (750 ml). The resultant suspension was stirred in an ice bath for 1 h and then filtered to give a solid (57.64 g). A portion of this solid (11.09 g) was dissolved in dichloromethane (307 ml) and ethanol (166 ml), boiled with decolourising charcoal for 10 min and then filtered. The dichloromethane was distilled off at atmospheric pressure until the temperature of the mixture was at 65°. The stirred mixture was cooled and the resulting precipitate was filtered off to give Compound X (9.28 g), t.l.c. (System A, 50:8:1) Rf 0.55.

$^1$H-n.m.r: 2.20(3H,s), 3.03(2H,t), 3.64(2H,m), 3.71(3H, s), 4.50(2H,s), 7.19(2H,m), 7.44(1H,s), 7.50(1H,d), 7.99 (1H,d), 11.76(1H,s).

EXAMPLE 2

Hydrogen chloride gas (1 g) was bubbled into N-methylpyrrolidinone (10 ml). To this solution was added Intermediate 1 (2 g) and Intermediate 2 (0.74 g), and the solution was heated to ca. 130° under nitrogen. After 30 min, a further portion of Intermediate 2 (0.74 g) was added and heating was continued for a further 4 h. The solution was allowed to cool, added to water (30 ml) and 1M sodium bicarbonate solution (40 ml) added to pH 7–8. After standing for 2 h, the precipitated solid was filtered off, washed with water (2×10 ml) and dried in vacuo at 40° to give Compound X (1.3 g), t.l.c. (System A, 50:8:1) Rf 0.59. The $^1$H-n.m.r. data for this material were consistent with those obtained for the product of Example 1.

EXAMPLE 3

A mixture of Intermediate 1 (2.00 g), Intermediate 2 (2.97 g) and p-toluenesulphonic acid monohydrate (0.48 g) in xylene (24 ml) was stirred and heated to reflux over 0.75 h. The reaction mixture was heated at reflux, with stirring, for a further 4 h, then cooled to ambient temperature. The solvent was decanted and the residual semi-solid was triturated with xylene (20 ml). The xylene was decanted and the residue was dissolved in water (20 ml). The solution was treated with 2N sodium hydroxide (to pH 14). A gum was deposited which was triturated with water (20 ml) and ethanol (15 ml) to give Compound X (1.30 g). The t.l.c. data for this material were consistent with those obtained for the product of Example 1.

EXAMPLE 4

A mixture of Intermediate 1 (1.50 g) and Intermediate 2 (1.89 g) in glacial acetic acid (10 ml) was stirred and heated to reflux over 0.75 h, then heated at reflux for 5.25 h, during which time a further portion of Intermediate 2 (1.63 g) was added. The reaction mixture was cooled to 40° and basified (to pH 14) with 5N sodium hydroxide (35 ml). The mixture was saturated with solid potassium carbonate and extracted with a mixture of ethyl acetate and ethanol (1:1; 100 ml). Evaporation of the extracts gave a gum which was purified by FCC eluting with ethyl acetate/methanol (4:1) to give Compound X (0.70 g). The $^1$H-n.m.r. and t.l.c. data for this material were consistent with those obtained for the product of Example 1.

EXAMPLE 5

A mixture of Intermediate 1 (1.50 g), Intermediate 2 (1.89 g) and p-toluenesulphonic acid monohydrate (0.29 g) in 1-butanol (10 ml) was stirred and heated to reflux over 1 h, then heated at reflux for a further 23 h, during which time a further portion of Intermediate 2 (1.89 g) was added. The reaction mixture was cooled to ambient temperature, treated with water (10 ml) and then with 8% aqueous sodium bicarbonate (20 ml). The mixture was cooled to 5° and treated with ethyl acetate (25 ml). The resulting suspension was filtered and the residue was washed with water to give Compound X (1.51 g). The $^1$H-n.m.r. and t.l.c. data for this material were consistent with those obtained for the product of Example 1.

EXAMPLE 6

A mixture of Intermediate 1 (1.50 g), Intermediate 2 (2.50 g) and p-toluenesulphonic acid monohydrate (0.38 g) in dimethylacetamide (10 ml) was stirred and heated to 125° over 0.5 h, then heated at 125° for a further 3.75 h, during which time a further portion of Intermediate 2 (0.50 g) was added. The reaction mixture was cooled to ambient temperature, treated with water (10 ml) and then, dropwise with stirring, with 8% aqueous sodium bicarbonate (20 ml). The resultant suspension was cooled to 5° and filtered to give a solid which was washed with water to give Compound X (1.54 g). The $^1$H-n.m.r. and t.l.c. data for this material were consistent with those obtained for the product of Example 1.

EXAMPLE 7

A mixture of Intermediate 1 (1.50 g), Intermediate 2 (2.08 g) and concentrated hydrochloric acid (0.4 ml) in 1-methyl-2-pyrrolidinone (10 ml) was stirred and heated to 115° over 0.5 h, then heated at 115–120° for 3.5 h. The reaction mixture was cooled to ambient temperature, treated with water (10 ml) and then with 8% aqueous sodium bicarbonate (28 ml). The resultant suspension was cooled to 5° and filtered to give a solid which was washed with water to give Compound X (1.58 g). The $^1$H-n.m.r. and t.l.c. data for this material were consistent with those obtained for the product of Example 1.

EXAMPLE 8

A mixture of Intermediate 1 (1.50 g), Intermediate 2 (1.89 g) and methanesulphonic acid (0.19 g) in 1-methyl-2-pyrrolidinone (10 ml) was stirred and heated to 123° over 0.8 h, then heated at 117–124° for 1 h. The reaction mixture was cooled to ambient temperature, treated with water (6 ml) and then with 8% aqueous sodium bicarbonate (20 ml), dropwise with stirring. The resultant suspension was cooled to 2° and filtered to give a solid which was washed with water to give Compound X (1.47 g). The $^1$H-n.m.r. and t.l.c. data for this material were consistent with those obtained for the product of Example 1.

EXAMPLE 9

A mixture of Intermediate 1 (1.50 g), Intermediate 2 (1.89 g) and maleic acid (0.20 g) in 1-methyl-2-pyrrolidinone (10 ml) was stirred and heated to 124° over 0.75 h, then heated at 112–125° for 2.25 h. The reaction mixture was cooled to ambient temperature, treated with water (6 ml) and then with 8% aqueous sodium bicarbonate (22 ml), dropwise with stirring. The resultant suspension was cooled to 5° and filtered to give a solid which was washed with water and ethanol to give Compound X (1.03 g). The $^1$H-n.m.r. and t.l.c. data for this material were consistent with those obtained for the product of Example 1.

EXAMPLE 10

A mixture of Intermediate 1 (1.50 g) and Intermediate 2 (1.89 g) in 1-methyl-2-pyrrolidinone (10 ml) was stirred and heated to 113° over 0.5 h, then heated at 113–126° for 1.2 h. The reaction mixture was cooled to ambient temperature and treated with water (6 ml), followed by 8% aqueous sodium bicarbonate (20 ml), dropwise with stirring. The resultant suspension was cooled to 5° and filtered to give a solid which was washed with water and ethanol to give Compound X (1.05 g). The $^1$H-n.m.r. and t.l.c. data for this material were consistent with those obtained for the product of Example 1.

EXAMPLE 11

A mixture of Intermediate 1 (10.0 g), Intermediate 1 (13.4 g) and p-toluenesulphonic acid monohydrate (2.38 g) in 1-methyl-2-pyrrolidinone (40 ml) was stirred and heated to 128° over 0.75 h, then heated at 122–140° for a further 1.1 h. The reaction mixture was then cooled to 5° and filtered to give a solid which was washed with ethanol to give Compound X in the form of its hydrochloride salt (9.95 g), m.p. 281–282° (dec.). The t.l.c. data for this material were consistent with those obtained for the product of Example 1.

We claim:

1. A process for the preparation of a compound of formula (I):

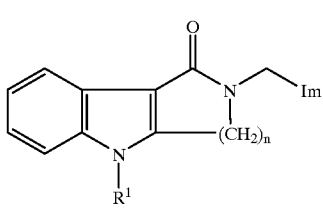

(I)

wherein Im represents an imidazolyl group of the formula:

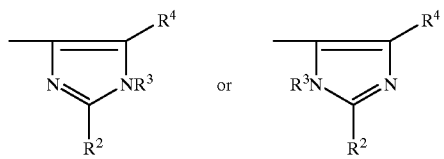

and R¹ represents a hydrogen atom or a methyl, ethyl, n-propyl or isopropyl group, $R^2$ and $R^3$ each represent a hydrogen atom, $R^4$ represents a methyl group; and n represents 2; or a physiologically acceptable salt or solvate thereof;

which comprises reacting a compound of formula (II)

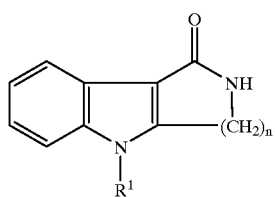

(II)

or a protected derivative thereof, with a compound of formula (III):

HOCH₂-Im        (III)

or a salt thereof in the presence of an acid which is a strong mineral acid or a hydrocarbylsulphonic acid at a temperature of from 100 to 200° C. in a high boiling polar solvent, followed where necessary by removal of any protecting groups.

2. A process according to claim 1 for the preparation of 2,3,4,5-tetrahydro-5-methyl-2-[(5-methyl-1H-imidazol-4-yl)methyl]-1H-pyrido[4,3-b]indol-1-one by reaction of 2,3,4,5-tetrahydro-5-methyl-1H-pyrido[4,3-b]indol-1-one as the compound of formula (II) and 4-hydroxymethyl-5-methylimidazole as the compound of formula (III), the compound of formula (III) optionally being used in the form of the hydrochloride salt.

3. A process according to claim 1 in which the reaction is carried out in N-methylpyrrolidinone or dimethylacetamide.

4. A process according to claim 1 in which the reaction is carried out in water or an alcohol at the reflux temperature of the solvent.

5. A process according to claim 1 in which the compound of formula (I) produced is subsequently converted into a salt.

6. A process according to claim 5 in which the compound of formula (I) is converted into the hyrdochloride.

7. A process for the preparation of a compound of formula (I):

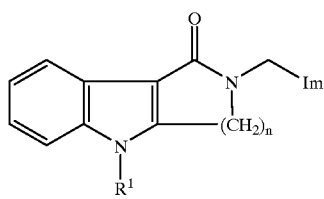

(I)

wherein Im represents an imidazolyl group of the formula:

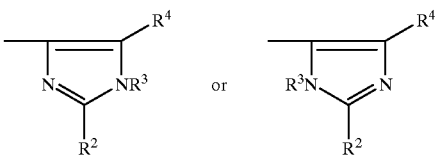

and R¹ represents a hydrogen atom or a methyl, ethyl, n-propyl or isopropyl group, $R^2$ and $R^3$ each represent a hydrogen atom, $R^4$ represents a methyl group; and n represents 2; or a physiologically acceptable salt or solvate thereof;

which comprises reacting a compound of formula (II)

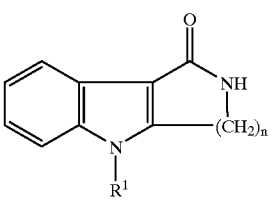

(II)

or a protected derivative thereof, with a compound of formula (III):

HOCH₂-Im        (III)

or a salt thereof in the presence of p-toluenesulphonic acid at a temperature of from 100 to 200° C. in a high boiling polar solvent, followed where necessary by removal of any protecting groups.

8. A process for the preparation of a compound of formula (I):

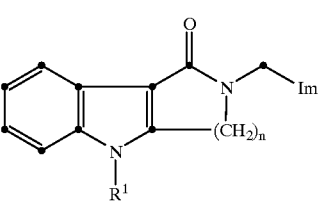

(I)

wherein Im represents an imidazolyl of the formula:

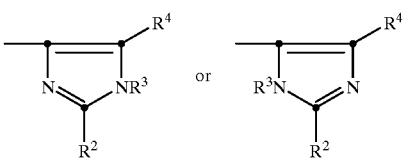

and R¹ represents a hydrogen atom or a methyl, ethyl, n-propyl or isopropyl group, $R^2$ and $R^3$ each represent a hydrogen atom, $R^4$ represents a methyl group; and n represents 2; or a physiologically acceptable salt or solvate thereof;

which comprises reacting a compound of formula (II)
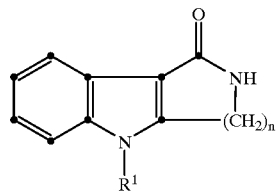
(II)
with a compound of formula (III):
HOCH$_2$-Im   (III)
or a salt thereof in the presence of an acid which is methanesulphonic acid at a temperature of from 100 to 200° C in a high boiling polar solvent, followed where necessary by removal of any protecting groups.
* * * * *